| United States Patent [19] | [11] 4,077,795 |
|---|---|
| Cooke et al. | [45] * Mar. 7, 1978 |

[54] METHOD FOR INHIBITING THE GROWTH OF TOBACCO SUCKERS

[75] Inventors: Anson Richard Cooke, Hatfield; George Robert Starke, Perkasie, both of Pa.

[73] Assignee: Union Carbide Corporation, New York, N.Y.

[*] Notice: The portion of the term of this patent subsequent to Apr. 29, 1992, has been disclaimed.

[21] Appl. No.: 549,246

[22] Filed: Feb. 12, 1975

Related U.S. Application Data

[63] Continuation-in-part of Ser. No. 282,879, Aug. 22, 1972, Pat. No. 3,880,643, which is a continuation-in-part of Ser. No. 107,598, Jan. 18, 1971, abandoned.

[51] Int. Cl.² .............................................. A01N 9/20

[52] U.S. Cl. ............................................. 71/78; 71/121; 260/577

[58] Field of Search ............................................. 71/78

[56] References Cited

U.S. PATENT DOCUMENTS

| 3,111,403 | 11/1963 | Soper | 71/121 |
|---|---|---|---|
| 3,332,769 | 7/1967 | Soper | 71/121 |
| 3,672,866 | 6/1972 | Damiano | 71/121 |

FOREIGN PATENT DOCUMENTS

| 2,232,263 | 1/1973 | Germany | 71/78 |
|---|---|---|---|

Primary Examiner—Elbert L. Roberts
Assistant Examiner—Catherine L. Mills
Attorney, Agent, or Firm—Robert C. Brown

[57] ABSTRACT

The growth of tobacco suckers in tobacco plants is inhibited by applying to the tobacco plants an effective amount of a substituted 2,6-dinitroaniline alone or in combination with a surfactant.

18 Claims, No Drawings

METHOD FOR INHIBITING THE GROWTH OF TOBACCO SUCKERS

This application is a continuation-in-part application of Application Ser. No. 282,879, filed Aug. 22, 1972 now U.S. Pat. No. 3,880,643 which is a continuation-in-part application of Ser. No. 107,598 filed Jan. 18, 1971, now abandoned.

BRIEF DESCRIPTION OF THE INVENTION

This invention relates to a method for controlling the growth of suckers in tobacco plants by spraying the tobacco plants shortly after topping with a solution containing an effective amount of a 2,6-dinitroaniline derivative alone or in combination with a surfactant.

Preferably the dinitroaniline is a compound of the formula:

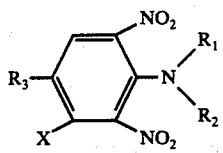

wherein $R_1$ and $R_2$ are each independently selected from the group consisting of:
 (a) hydrogen,
 (b) lower alkyl,
 (c) halosubstituted lower alkyl,
 (d) lower alkenyl,
 (e) alkoxy-lower alkyl, and
 (f) monocycloalkyl-lower alkyl with the proviso that only one of $R_1$ and $R_2$ can be branched lower alkyl or branched lower alkenyl;
wherein $R_3$ is selected from the group consisting of:
 (a) halo,
 (b) lower alkyl,
 (c) halo substituted-lower alkyl,
 (d) methyl sulfonyl, and
 (e) sulfanilamide;
wherein X is selected from the group consisting of:
 (a) hydrogen,
 (b) halo,
 (c) amino,
 (d) lower alkyl,
 (e) mono-lower alkyl amino, and
 (f) alkoxy;
with the proviso that there can only be one hydrogen group on the compound, except that there can be two hydrogen groups when:
 (a) X is hydrogen, and
 (b) i. $R_2$ is alkoxy-lower alkyl or ii. $R_3$ is halo substituted lower alkyl.

BACKGROUND OF THE INVENTION

While methods of culture of tobacco differ somewhat in different regions and with various tobacco types, the essential features are much the same.

Seedlings are produced in hotbeds and about 6 to 10 weeks after germination, when they are about 4 to 6 inches in height, the seedlings are transplanted to fields, either by hand or by machine. The distance of planting varies according to the type of tobacco. The rows are generally 3 to 4 feet apart with plants spaced at a distance of 12 to 48 inches in the row. Cigar and burley tobacco are commonly spaced 3 to 3½ feet by 12 to 27 inches, while fire-cured tobacco is planted in hills which may be as much as four feet apart. Maryland tobacco is transplanted in hills 34 × 34 inches or closer, while flue-cured tobacco is spaced 2' × 4'.

As a general rule when the plant has attained the desired size, usually at or before attaining flowering, it is debudded or topped; that is, the terminal growth is removed. The number of leaves remaining on each plant commonly varies from 16 to 20 with the cigar, Maryland, burley and flue-cured types and 10 to 14 leaves with fire-cured and dark air-cured tobacco.

Following topping, suckers or lateral shoots develop along the stem and must be removed at more or less frequent intervals, in order to increase leaf development. Topping is generally accomplished by mechanical means which involves removing or cutting away the stem apex, including flowers and some top leaves. This process is usually carried out near the stage of plant maturity, in order to stimulate development of the remaining leaves and to obtain the desirable physical and chemical properties for choice tobaccos. By removing the apex at flowering, the maximum number of harvestable leaves is present and the plant can then divert most of its energy into stimulating the development of these remaining leaves.

When the apex is left intact, most of the plant's energy is diverted to the flowering process, thus preventing expansion of leaves and decreasing yields. However, when the apex is removed, this phenomenon of apical dominance is destroyed with a resulting stimulation of lateral bud or "sucker" growth from the leaf axils. Thus, where only one apex was present, there are now five to ten apices present, which, if left uncontrolled, will further reduce yields. These axillary buds or suckers start to develop soon after the topping operation and prior to the discovery of sucker control agents, these suckers had to be continuously removed by hand to achieve the purpose of topping, since otherwise the suckers themselves would grow at the expense of the development of the desired leaves.

The earliest and perhaps even now, the most common method of controlling the growth of these suckers is to remove them by hand when they are 4 to 6 inches in length. Since the developing suckers are not all in the same stage of growth, the field must be gone over four to six times. It is, therefore, evident that with the increasing cost and decreasing supply of available hand labor, more efficient methods are necessary for control.

The need for commercial chemical tobacco sucker control agents developed as a result of the importance of this cultural practice of topping or removing the apex of the developing tobacco plant when in flower. Certain known chemical products when applied will inhibit the development of suckers or when applied to growing suckers will cause them to wither and inhibit further growth of the suckers. Even now, however, no entirely satisfactory method of sucker control has been developed.

The first attempts made at sucker control by chemical means were through the use of various mineral oil emulsions as well as car and used diesel oils. These compounds are quite injurious to leaf tissue and as a result had to be hand-applied to the cut stalk of each individual plant. Since these materials function mainly through contact activity, volume per plant is critical.

With the discovery and development of maleic hydrazide (MH-30), this compound today is probably the most widely used agent for controlling sucker growth. It is material which is readily translocated within plants and is active in inhibiting cell division in meristematic areas but not cell enlargement. Both timing and environmental conditions are important for maximum effectiveness. If applied too soon after topping, normal leaf expansion will not occur, thus reducing yields. If relative humidity is low or plants are in a wilted state, absorption and effectiveness are greatly reduced. The compound also reduces the specific volume or "filling power" as well as increasing the moisture absorption of the leaf.

The newest agents for sucker control are the fatty alcohols and fatty acid amines. These materials are contact in action; that is, they must come in direct contact with each axillary bud. Control is achieved by selectively killing the primary axillary bud meristem without damaging mature leaf tissue. Since no translocation occurs, subsequent axillary buds will develop into suckers. Therefore, commercial control is only achieved for a matter of 1 to 2 weeks. In practice, these compounds have been shown to injure leaf tissue if recommended application methods are not followed closely. It is also evident that volume per plant is critical to insure complete contact with each leaf axil. Where chemical sucker control agents are used, they are also sometimes unsuitable for the reason that they provide inadequate inhibition of sucker development or cause metabolic changes other than inhibition of suckers, which metabolic changes are undesirable in the tobacco plant. Moreover, there is also the question of the possibility of undesirable residues in the leaf tissue. It is, therefore, an object of this invention to provide new and suitable chemical control of tobacco sucker growth without the disadvantages of prior art chemical treatments.

DETAILED DESCRIPTION OF THE INVENTION

This invention relates to chemical control of tobacco suckers by treating the tobacco plant with a 2,6-dinitroaniline derivative. More particularly, this invention relates to the use of a compound of the formula:

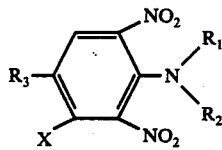

Formula I wherein $R_1$ and $R_2$ are each independently selected from the group consisting of:
(a) hydrogen,
(b) lower alkyl,
(c) halo-substituted lower alkyl,
(d) lower alkenyl,
(e) alkoxy-lower alkyl, and
(f) monocycloalkyl--lower alkyl with the proviso that only one of $R_1$ and $R_2$ can be branched lower alkyl or branched lower alkenyl;
wherein $R_3$ is selected from the group consisting of:
(a) halo,
(b) lower alkyl,
(c) halo substituted-lower alkyl,
(d) methylsulfonyl, and
(e) sulfanilamide;
wherein X is selected from the group consisting of:
(a) hydrogen,
(b) halo,
(c) amino,
(d) lower alkyl,
(e) monolower alkyl amino,
(f) alkoxy;
with the proviso that there can only be one hydrogen group on the compound, except that there can be two hydrogen groups when:
(a) X is hydrogen, and
(b) i. $R_2$ is alkoxy lower alkyl, and ii. $R_3$ is halo substituted lower alkyl.

As used herein, the term lower alkyl represents straight or branched chain hydrocarbons having 1 to 7 carbons. The term lower alkenyl represents straight or branched chain aliphatic hydrocarbons containing 2 to 7 carbon atoms and at least 1 double bond. In the case where $R_1$ and $R_2$ are both lower alkyl or lower alkenyl, at least one or $R_1$ and $R_2$ is a straight chain lower alkyl or lower alkenyl and preferably $R_1$ and $R_2$ together have no more than 8 carbon atoms total.

Halo-substituted lower alkyl includes lower alkyl groups having one or more hydrogens replaced by halogen which can be on the same or different carbon atoms in the alkyl groups such as, for example, chloromethyl, bromomethyl, dichloromethyl, a,a-dichloroethyl, trichloromethyl, β-chloroethyl, trifluoromethyl and the like.

The term mono cycloalkyl, as used herein, denotes monocyclic hydrocarbons containing 3 to 6 carbon atoms, such as, for example, cyclopropyl, cyclopenthyl, cyclohexyl and the like.

The term mono cycloalkyl-lower alkyl denotes lower alkyl groups in which a hydrogen on one of the carbon atoms has been replaced by a cycloalkyl group, as defined above, such as cyclopropylmethyl and the like.

The term halo, as used herein, includes all four halogens, namely chlorine, bromine, iodine and fluorine with chlorine and fluorine being the preferred halogens.

The term alkoxy, as used herein, is a lower alkyloxy group wherein lower alkyl is as defined above.

The term alkoxy-lower alkyl, as used herein, denotes an alkyl group in which one or more hydrogens is replaced by an alkoxy group as defined hereinabove.

The term aralkyl, as used herein denotes an alkyl group in which one or more hydrogens is replaced by phenyl, such as benzyl, phenthyl, phenylpropyl and the like.

The term alkaryl denotes an aryl group in which one or more hydrocarbons is replaced with an alkyl substituent.

The term methylsulfonyl, as used herein, denotes a group of the formula:

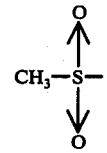

The term sulfanilamide, as used herein, denotes a group of the formula:

$NH_2$—$SO_2$—

The term amino, as used herein, denotes a group of the formula $NH_2$—.

The term monoloweralkyl amino, as used herein denotes an amino group wherein one hydrogen is substituted by a lower alkyl group.

The compounds of Formula I which are useful in the practice of the process of this invention are generally known compounds or readily obtained derivatives of known compounds. All of these compounds are readily obtainable by conventional synthesis methods well known to those skilled in the art. Preparative methods for synthesizing compounds of Formula I are disclosed, for example, in the following U.S. Patents which are all hereby incorporated by reference.

U.S. Pat. Nos. 3,257,190 and 3,403,180 disclose the preparation of dinitroanilines of the type employed for use in the method of this invention wherein $R_1$ and $R_2$ in Formula I above can be $C_1$ to $C_5$ alkyl, $C_2 - C_5$ alkenyl, halo-substituted $C_2 - C_5$ alkyl or alkoxy lower alkyl and $R_3$ is hydrogen, alkyl, alkoxy, dialklcarbamyl, halo or halo alkyl. Representative compounds of this group are, for example:
N,N-di-n-propyl-3-chloro-2,6-dinitroaniline;
N,N-di-n-butyl-4-fluoro-2,6-dinitroaniline;
N,N-diethyl-4-trichloromethyl-2,6-dinitroaniline;
N-ethyl-N-n-butyl-2,6-dinitroaniline;
N-methyl-N-n-propyl-2,6-dinitro-p-toluidine;
N-N-di-n-propyl-2,6-dinitroaniline;
N,N-di-n-propyl-4-isopropyl-2,6-dinitroaniline;
N-n-propyl-N-n-butyl-4(3-bromopropyl)-2,6-dinitroaniline;
N-ethyl-N-n-propyl-4-isopropyl-2,6-dinitroaniline;
N,N-di-n-propyl-4-bromo-2,6-dinitroaniline;
N,N-diethyl-4-(2-chloroethyl)-2,6-dinitroaniline;
N,N-di-n-propyl-4-trifluoromethyl-2,6-dinitroaniline; (trifluralin)
N-ethyl-N-n-butyl-4-trifluoromethyl-2,6-dinitroaniline;
N,N-dimethyl-4-trifluoromethyl-2,6-dinitroaniline;
N-methyl-N-alkyl-4-trifluoromethyl-2,6-dinitroaniline;
N,N-di-(3-butynyl)-4-trifluoromethyl-2,6-dinitroaniline;
N-methyl-N-iso-butyl-4-trifluoromethyl-2,6-dinitroaniline;
N-ethyl-N-iso-butyl-4-trifluoromethyl-2,6-dinitroaniline;
N-n-butyl-N-n-propyl-4-trifluoromethyl-2,6-dinitroaniline;
N-methyl-N-n-propyl-4-trifluoromethyl-2,6-dinitroaniline;
N-methyl-N-allyl-4-trifluoromethyl-2,6-dinitroaniline;
N,N-di-n-butyl-4-trifluoromethyl-2,6-dinitroaniline;
N-allyl-N-ethyl-4-trifluoromethyl-2,6-dinitroaniline;

U.S. Pat. No. 3,321,292 discloses the preparation of dinitroanilines of the type employed for use in the practice of this invention wherein $R_3$ in Formula I above is methylsulfonyl and $R_1$ and $R_2$ can be alkyl or alkenyl. Representative compounds of this group are, for example:
4-(methylsulfonyl)-2,6-dinitro-N,N-diethylaniline;
4-(methylsulfonyl)-2,6-dinitro-N,N-dipropylaniline;
4-(methylsulfonyl)-2,6-dinitro-N,N-dibutylaniline;
4-(methylsulfonyl)-2,6-dinitro-N-ethyl, N-propylaniline;
4-(methylsulfonyl)-2,6-dinitro-N-ethyl, N-butylaniline;
4-(methylsulfonyl)-2,6-dinitro-N-propyl, N-butylaniline;
4-(methylsulfonyl)-2,6-dinitro-N-vinyl, N-ethylaniline;
4-(methylsulfonyl)-2,6-dinitro-N-vinyl, N-propylaniline;
4-(methylsulfonyl)-2,6-dinitro-N,N-diallylaniline;
4-(methylsulfonyl)-2,6-dinitro-N-allyl, N-ethylaniline;
4-(methylsulfonyl)-2,6-dinitro-N-allyl, N-propylaniline;
4-(methylsulfonyl)-2,6-dinitro-N-allyl, N-butylaniline;
4-(methylsulfonyl)-2,6-dinitro-N-(2-methallyl), N-ethylaniline;
4-(methylsulfonyl)-2,6-dinitro-N-(2-methallyl), N-propylaniline;
4-(methylsulfonyl)-2,6-dinitro-N-butenyl, N-allylaniline;
4-(methylsulfonyl)-2,6-dinitro-N-butenyl, N-propylaniline.

U.S. Pat. No. 3,546,295 discloses the preparation of dinitroanilines of the type employed for use in the practice of this invention wherein $R_3$ in Formula I above is hydrogen, alkyl, trifluoromethyl or alkylsulfonyl and $R_1$ and $R_2$ can be cycloalkyl, alkenyl or cyclo alkylalkyl.

U.S. Pat. Nos. 3,332,769 and 3,111,403 disclose the preparation of dinitroanilines of the type employed for use in the method of this invention wherein one of $R_1$ and $R_2$ in Formula I above is hydrogen and the other can be a straight or branched chain alkyl group and $R_3$ is hydrogen, alkyl, halogen or haloalkyl. Representative compounds of this group are, for example:
N-(sec-butyl)-2,6-dinitro-4-fluoroaniline;
N-(3-pentyl)-2,6-dinitro-4-trifluoromethylaniline;
N-(isopropyl)-2,6-dinitro-4-chloroaniline;
N-4-(di-isopropyl)-2,6-dinitroaniline;
N-(4-methyl-3-hexyl)-2,6-dinitro-4-bromoaniline;
N-(2-heptyl)-2,6-dinitro-p-toluidine;
N-(4-methyl-2-pentyl)-2,6-dinitro-4-ethylaniline;
N-(isopropyl)-2,6-dinitroaniline;
N-(3-pentyl)-2,6-dinitroaniline;
2,6-dinitroaniline;
4-methyl-2,6-dinitroaniline;
N-ethyl-4-ethyl-2,6-dinitroaniline;
N-methyl-4-isopropyl-2,6-dinitroaniline;
4-chloro-2,6-dinitroaniline;
N-n-propyl-4-trifluoromethyl-2,6-dinitroaniline;
4-n-butyl-2,6-dinitroaniline.

Compounds not specifically disclosed in these references can be reaily prepared by analogous procedures utilizing the ordinary skill of the art. In particular, a specifically effective tobacco sucker control agent, as disclosed in this invention, is the compound 4-t-butyl-N-sec-butyl-2,6-dinitroaniline which is easily prepared by the following reaction sequence.

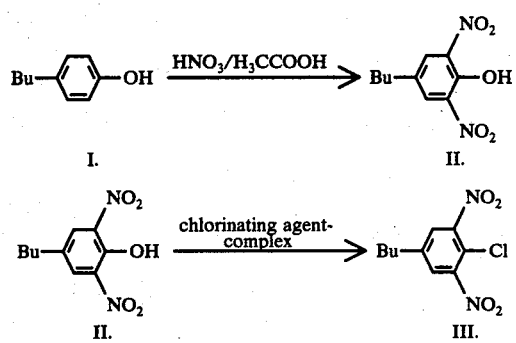

The compound is preferably used at a rate of about 1 to 3 lbs. active material per acre of tobacco in between about 50 to 200 gallons of water. Greater or lesser amounts can, of course, be utilized depending on individual circumstances and the material can also be applied in more or less concentrated form depending upon the mode of application. The compounds of Formula I are preferably used in formulation with a wetting agent, particularly a non-ionic or an anionic wetting agent. Such a wetting agent may perform its conventional function of reducing the surface tension of the solution of the active sucker control compound in water, thereby increasing effective application of the solution to the plant surfaces. It is clear, however, as is shown by the test results described hereinbelow, that such a wetting agent significantly enhances the tobacco sucker controlling activity of the dinitroaniline derivative compositions of this invention, while possessing no such controlling activity by itself. Any of the conventional wetting agents, such as the alkanol amines, alkylsulfonates, sulfonated amines and amides, ethoxylated alcohols and the ethoxylated alkyl phenols, ethoxylated amines and amides, ethoxylated fatty acids, ethoxylated fatty esters and oils, glycerol esters, phosphate derivatives, and others as well as mixtures of any of these can be utilized.

Particularly suitable wetting agents are, for example, the Atlox surfactants prepared and sold by Atlas Chemical Industries, Inc., Wilmington, Delaware; the Gafac, Igepal and Emulphor surfactants manufactured and sold by GAF Corporation, 140 West 51st Street, New York, New York. The sulfonics manufactured and sold by the Jefferson Chemical Company, 1121 Walker Avenue, Houston, Texas; the Agrimuls, Lomar and Sellogen surfactants sold by Nopco Chemical Division, Diamond Shamrock Chemical Company; the Tritons manufactured and sold by Rohm and Haas Company, Independence Mall, West, Philadelphia, Pennsylvania; the Toximul surfactants sold by Stepan Chemical Company, Worthfield, Illinois; the T-mulz surfactants sold by Thompson-Hayward Chemical Company, Kansas City, Kansas; and the Emcol surfactants manufactured and sold by Witco Chemical Company, Inc., 122 East 42nd Street, New York, New York. Other wetting agents can, of course, be used with equivalent results. Particularly good results have been obtained with the surfactant Triton-X-100 supplied by Rohm and Haas and the surfactant X-77 supplied by Colloidal Products.

The amount of surfactant used is not critical, though, ordinarily, it should not be used in amounts greater than about 2% by volume of the final spray solution, since higher amounts could cause leaf burn, depending upon the particular surfactant employed. Preferably, the surfactant will comprise about 0.1 to about 1.0% of the final spray volume and generally less than 0.5% will be sufficient. In the preparation of liquid concentrates or suspensions or wettable powder concentrates, the surfactant will ordinarily be present in the formulated concentrate in amounts between about $\frac{1}{3}$ to about 3 times the amount of active ingredient. In addition to the active material of Formula I and, if desired, a suitable surfactant liquid, solid or paste formulations in concentrate or ready-to-use form can be prepared by methods known to the art employing conventional adjuvants, such as finely divided solid carrier materials, e.g., talc, clays, flour, etc.; solubilizing agents, e.g., silicates, carbonates, etc.; non-aqueous liquids, such as aliphatic and aromatic hydrocarbons; binding agents or adhesives, such as rosin, albumen, etc.; thickening agents, such as gums and the like; anti-foaming agents, such as nonyl carbinol (decanol), etc., or other conventional excipients.

The compositions can, if desired, be formulated with other compatible active ingredients, such as insecticides, fungicides, and the like. The dinitroaniline derivatives can also be formulated with other tobacco sucker control agents, such as maleic hydrazide, tertiary or secondary fatty amine salts, $C_6$ to $C_{18}$ saturated and unsaturated fatty acid esters, and $C_6$ to $C_{18}$ saturated fatty alcohols to form combination products useful in the method of the present invention. U.S. Pat. No. 3,223,517 discloses the use of tertiary or secondary fatty amine salts for controlling tobacco sucker growth. Examples of the amine salts are dodecyldimethylamine acetate, dodecylmethylamine acetate, and cocodimethylamine acetate. U.S. Pat. No. 3,340,040 discloses the use of the lower alkyl esters of $C_6$ to $C_{18}$ saturated and unsaturated fatty acids for controlling tobacco sucker growth. Examples of the fatty acid esters which can be employed are methyl caproate, methyl caprylate, methyl caprate, methyl laurate, and methyl stearate. U.S. Pat. No. 3,438,765 discloses the use of $C_6$ to $C_{18}$ saturated fatty alcohols. Typical examples of suitable fatty alcohols which can be employed herein are n-octanol, n-decanol, n-dodecanol, n-hexadecanol, n-tetradecanol, and n-hexanol. These tobacco sucker control agents are generally known compounds which are readily obtainable commercially or by conventional synthesis methods well known to those skilled in the art. The foregoing U.S. Patents disclosing the use of particular tobacco sucker control agents, which can be combined with the dinitroaniline derivatives and employed in the practice of the process of this invention, are hereby incorporated by reference.

A surprising aspect of this invention is that by utilizing these combination products, better than additive results are obtained. It has been discovered that when employing the combination product, consisting of a 2,6-dinitroaniline derivative described herein and a tobacco sucker control agent selected from the group consisting of tertiary or secondary fatty amine, fatty acid ester, and fatty alcohol, on certain types of tobacco wherein higher rates of application are ordinarily necessary, the amount of each material employed to obtain the desired results is less than is necessary, should each material be used alone. The combination has appreciably greater activity, thereby allowing the application of lower dosages per acre.

The use of these admixtures results in uniform control which is effective for longer periods of time and, since less of the materials are employed, there is also less probability that metabolic changes will be caused and there will also be less residue in the leaf tissue.

When an admixture of the dinitroaniline derivative, in combination with an agent selected from the group consisting of tertiary or secondary fatty amines, fatty acids, fatty acid esters, and fatty alcohols, is employed, the ratio of the active ingredients can vary within a broad range. In general, the optimum ratio will depend upon the type of tobacco to be treated, and the specific fatty acid ester, fatty amine, or fatty alcohol and particularly the length of the aliphatic moiety. In general, the admixture should contain from about 1 to 10 parts by weight of the sucker agent selected from the group of tertiary and secondary fatty amine, fatty acid ester, and fatty alcohol, for each part by weight of dinitroaniline compound. In any given instance, the relative proportions of the active components utilized will vary, as noted above, upon the conditions of application. In all events, the combination has been found to result in better than additive effects than can be obtained when each material is separately employed. A preferred admixture which, when employed, will result in excellent sucker control contains 4-t-butyl-N-sec-butyl-2,6-dinitroaniline and a commercially available combination of $C_6$ to $C_{12}$ saturated fatty alcohols (OFF-SHOOT-T, prepared and sold by Proctor & Gamble Co., Cincinnati, Ohio), in a weight ratio of fatty alcohol to dinitroaniline from about 4:1 to about 8:1.

The rate of application of the admixture should be within the range of from about 1 to about 18 lb/A of active ingredient. In using the admixtures, they may be applied to the mature tobacco plants in the form of solutions, emulsions, suspensions, dust formulations, pastes, and the like, as described hereinabove. The most convenient method of application is an aqueous emulsion, as described hereinabove.

Should the agent to be mixed with the dinitroaniline derivative be insufficiently water soluble for convenient formulation into aqueous concentrations, a liquid emulsion can be prepared by dissolving both the dinitroaniline and the sucker control agent in a small amount of a nonphytotoxic solvent, then adding an emulsifier and water to form the ready-to-use composition. Alternatively, the agent to be mixed with the dinitroaniline derivative can be mixed with an emulsifier, thereafter adding said emulsion to the already prepared emulsion containing the dinitroaniline derivative, thereafter adding water to form the ready-to-use composition.

As described hereinbove, the amount of surfactant used in the admixture is not critical, although ordinarily it should not be used in amounts greater than about 2% by volume of the final spray solution. Preferably, the surfactant will comprise about 0.1 to about 1% of the final spray volume. In the preparation of liquid concentrates or suspensions or wettable powder concentrates, the surfactant will ordinarily be present in the formulated concentrate in amounts between about ⅓ to 3 times the amount of active ingredient.

The admixture used in the method of this invention can be employed as a liquid spray, at an effective volume of application, of the ready-to-use admixture composition, when applied directly to the locus to be treated or when employed as a directed foliar spray, of from about 50 to 200 gallons per acre. As stated hereinabove, any suitable formulation can be employed, such that the rate of application of active material is from about 1 to about 18 lbs. per acre in the form of the suitable aqueous solution, emulsion, dust formulation, or the like. The precise amount of active material applied will depend upon the degree of response which is desired.

The preparation and biological activity of the dinitroanilines and the combination products employed in the method of this invention will be more fully understood from the detailed tests and results described hereinbelow.

EVALUATION I

Greenhouse Tests

The tobacco plant chosen for assay work was the Xanthii type. This is a dwarf tobacco obtaining a maximum height under greenhouse conditions of about 5 to 6 feet. It is day-neutral, and grows well under both low and high light intensities. It is also one of the more sensitive types to various chemicals. Seed are sown in potting soil and covered lightly with sand. In two months, the seedlings have emerged and have 2 to 3 leaves. At this time, they are placed in 3-inch peat pots with potting soil. One month later, the plants have attained a height of 8 to 12 inches and are then placed in 7-inch pots with potting soil. Approximately two months later the plants have attained a height of 5 to 6 feet and have floral buds just beginning to open.

At this time, the apex of the plant is removed. Immediately after removing the apex, the test compounds are ready to be applied. The standard rate used is 100 mg active ingredient in 10 cc solvent per plant. Application is with a hand gun with 5-10 lbs. pressure. Approximately 8 cc of the spray is directed at the leaf axils with the remaining 2 cc applied over top and on the upper leaf surface to check for possible burn or other leaf injury. Three replications are generally used.

Immediately after spraying, the plants are placed in the greenhouse where they remain for a period of 2 to 3 weeks. After this time, observations are taken on number and length of resulting suckers and expressed as percentage of lateral buds inhibited from growing compared to topped checks. Also, leaf injury or other effects are also noted and recorded.

During the entire growing period, normal watering, fertilizing and insect control are practiced.

Results

The following table illustrates the activity obtained with several of the substituted dinitroanilines in greenhouse tests:

Table I

SUCKER CONTROL WITH SUBSTITUTED DINITROANILINES

| Chemical | Rate (mg/plant) | % Control |
|---|---|---|
| α,α,α-trifluoro-2,6-dinitro-N,N-dipropyl-p-toluidine | 100 | 98 |
| 4-(methylsulfonyl)-2,6-dinitro-N,N-dipropylaniline | 100 | 25 |
| 4-t-butyl-N-mono-sec-butyl-2,6-dinitroaniline | 100 | 99 |
| N-isopropyl-4-t-butyl-2,6-dinitroaniline | 100 | 92 |
| 4-t-butyl-N,N-diethyl-2,6-dinitroaniline | 100 | 90 |
| N-4-di-t-butyl-2,6-dinitroaniline | 100 | 85 |

EVALUATION II

Tobacco Sucker Control Assay of Dinitroaniline Derivatives

Representative dinitroaniline derivatives of Formula I were tested in tobacco sucker control assay according to the following method:

Tobacco plants (variety Xanthii) were grown in 7 inch pots until a height of approximately 2' was obtained. At this time, the apex was removed and chemicals were applied.

Materials were used for each treatment with a solvent system of 50% acetone plus 50% water. The amount of material per plant, as indicated in Table II, was applied with three replications. The spray was directed from the cut apex to allow maximum rundown along the stem.

Since the volume used did not provide for complete rundown, the readings were taken from the upper five leaf axils only.

Two weeks after treatment, a count was made of the number of suckers per plant over 1 inch in length along with the total weight per plant of these suckers. Results are expressed as percent reduction in fresh weight of the treatment compared to the control plants. Readings are averages of three replications per treatment with the checks being the average of six replications.

Table II

TOBACCO SUCKER CONTROL

Structure: 1,3-dinitro benzene with R3 at 4-position, X at 5-position, NR1R2 at 2-position; X is H

| R3 | R1 | R2 | Rate mg./Plant | % Tobacco Sucker Control |
|---|---|---|---|---|
| (CH3)3C— | H— | CH3CH2CH(CH3)— | 10 | 100 |
| (CH3)3C— | H— | (CH3)2CH— | 10 | 100 |
| (CH3)3C— | CH3CH2CH2— | CH3CH2CH2— | 10 | 100 |
| (CH3)3C— | CH3CH2— | CH3CH2— | 10 | 73 |
| (CH3)3C— | H— | CH3(CH2)2CH(CH3)— | 50 | 99 |
| (CH3)3C— | H— | CH3CH2— | 20 | 100 |
| (CH3)3C— | H— | CH3(CH2)2CH2— | 20 | 100 |
| (CH3)3C— | H— | (CH3O)2CH-CH2— | 20 | 100 |
| (CH3)3C— | H— | tetrahydrothiopyranyl (S-ring) | 20 | 100 |
| (CH3)3C— | CH3CH2— | CH3(CH2)2CH2— | 20 | 95 |
| (CH3)3C— | H— | cyclopropyl-CH2— | 20 | 100 |
| (CH3)3C— | H— | CH2=CHCH2— | 20 | 100 |
| (CH3)3C— | CH2=CHCH2— | CH2=CHCH2— | 20 | 98 |
| (CH3)3C— | H— | CH3O-CH(CH2CH2CH2—)— | 20 | 95 |
| (CH3)3C— | H— | cyclopropyl | 20 | 85 |
| (CH3)3C— | CH3— | (CH3CH2O)2CH-CH2— | 20 | 90 |
| (CH3)3C— | H— | CH3(CH2)4CH2— | 20 | 100 |
| (CH3)3C— | H— | H— | 20 | 99 |
| (CH3)3C— | H— | C6H5-CH2— | 20 | 100 |
| (CH3)3C— | H— | CH3CH2CH2— | 50 | 95 |
| (CH3)3C— | CH3— | CH3— | 20 | 98 |
| (CH3)3C— | H— | C6H5-CH(CH3)— | 20 | 100 |
| (CH3)3C— | H— | (o-CH2CH3-C6H4)-CH2— (?) | 20 | 80 |
| CH3CH2CH(CH3)— | H— | (CH3)2CH— | 10 | 100 |
| CH3CH2CH(CH3)— | H— | CH3CH2CH(CH3)— | 10 | 100 |
| CH3CH2CH(CH3)— | H— | CH3— | 20 | 100 |
| CH3CH2CH(CH3)— | H— | CH3CH2— | 20 | 100 |
| CH3CH2CH(CH3)— | CH3CH2— | CH3(CH2)2CH2— | 20 | 100 |
| CH3CH2CH(CH3)— | CH3CH2— | CH3CH2— | 20 | 100 |
| CH3CH2CH(CH3)— | CH3CH2CH2— | CH3CH2CH2— | 20 | 100 |
| CH3(CH2)2CH2— | CH3CH2CH2— | CH3CH2CH2— | 20 | 100 |

Table II-continued

TOBACCO SUCKER CONTROL

X is H

| $R_3$ | $R_1$ | $R_2$ | Rate mg./Plant | % Tobacco Sucker Control |
|---|---|---|---|---|
| $CH_3(CH_2)_2CH_2-$ | $H-$ | $CH_3CH_2CH(CH_3)-$ | 20 | 100 |
| $(CH_3)_2CH-$ | $H-$ | $CH_3CH_2CH(CH_3)-$ | 10 | 85 |
| $(CH_3)_2CH-$ | $CH_3CH_2CH_2-$ | $CH_3CH_2CH-$ | 20 | 99 |
| $(CH_3)_2CH-$ | $H-$ | $(CH_3)_2CH-$ | 40 | 90 |
| $(CH_3)_2CH-$ | $H-$ | $CH_3(CH_2)_2CH_2-$ | 40 | 85 |
| $CH_3CH_2C(CH_3)_2-$ | $H-$ | $H-$ | 20 | 100 |
| $CH_3CH_2C(CH_3)_2-$ | $H-$ | $(CH_3)_2CH-$ | 20 | 100 |
| $CH_3CH_2C(CH_3)_2-$ | $H-$ | $CH_3CH_2CH(CH_3)-$ | 20 | 100 |
| $CH_3CH_2C(CH_3)_2-$ | $CH_3-$ | $CH_3-$ | 20 | 100 |
| $CH_3CH_2C(CH_3)_2-$ | $CH_3CH_2-$ | $CH_3CH_2-$ | 20 | 98 |
| $CH_3CH_2C(CH_3)_2-$ | $CH_3CH_2CH_2-$ | $CH_3CH_2CH_2-$ | 20 | 98 |
| $CH_3CH_2C(CH_3)_2-$ | $H-$ | $CH_3-$ | 20 | 100 |
| $CH_3CH_2C(CH_3)_2-$ | $H-$ | $CH_3CH_2-$ | 20 | 75 |
| $CH_3CH_2C(CH_3)_2-$ | $H-$ | tetrahydrothiopyranyl | 20 | 95 |
| $CH_3-$ | $H-$ | $H-$ | 20 | 98 |
| $CH_3-$ | $CH_3CH_2CH_2-$ | $CH_3CH_2CH_2-$ | 20 | 99 |
| $CH_3-$ | $H-$ | $CH_3(CH_2)_4CH_2-$ | 50 | 100 |
| $CH_3-$ | $H-$ | tetrahydrothiopyranyl | 20 | 100 |
| $CH_3-$ | $ClCH_2CH_2-$ | $ClCH_2CH_2-$ | 50 | 99 |
| $CF_3-$ | $CH_3(CH_2)_2CH_2-$ | $CH_3CH_2-$ | 20 | 100 |
| $CF_3-$ | $CH_3CH_2CH_2-$ | $CH_3CH_2CH_2-$ | 10 | 100 |
| | | | 1 | 38 |
| $CF_3-$ | $ClCH_2CH_2-$ | $CH_3CH_2CH_2-$ | 5 | 86 |
| | | | 1 | 59 |
| $CF_3-$ | $CH_3CH_2CH_2-$ | cyclopropyl-$CH_2-$ | 5 | 93 |
| $CF_3-$ | $H-$ | $CH_3CH_2CH(CH_3)-$ | 50 | 98 |
| $CH_3SO_2-$ | $CH_3CH_2CH_2-$ | $CH_3CH_2CH_2-$ | 100 | 25 |
| $NH_2SO_2-$ | $CH_3CH_2CH_2-$ | $CH_3CH_2CH_2-$ | 1 | 19 |
| | | | 5 | 44 |

The same tobacco sucker control assay was performed with 3-substituted dinitroaniline derivatives.

Table IIa
TOBACCO SUCKER CONTROL

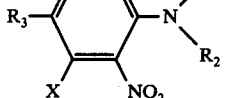

| $R_3$ | $R_1$ | $R_2$ | X | Rate mg./Plant | % Tobacco Sucker Control |
|---|---|---|---|---|---|
| Cl— | $CH_3CH_2CH_2$— | $CH_3CH_2CH_2$— | $CH_3$— | 10 | 81 |
| $(CH_3)_3C$— | H— | $CH_3CH_2CH$—<br>\|<br>$CH_3$ | $NH_2$— | 50 | 20 |

EVALUATION III

Representative 3-substituted dinitroaniline derivatives were tested in tobacco sucker control assays according to the method of Evaluation II, with the addition of a surfactant, e.g., Triton X-100, at .1% volume to the formulation applied to the tobacco plant.

Table III
TOBACCO SUCKER CONTROL

| $R_3$ | $R_1$ | $R_2$ | X | Rate mg./Plant | Tobacco Sucker Control |
|---|---|---|---|---|---|
| Cl— | H— | $CH_3CH_2$— | $CH_3$— | 20 | 100 |
| Cl— | H— | $CH_3$<br>\|<br>$CH$—$CH_2$—<br>\|<br>$CH_3$ | $CH_3$— | 20 | 100 |
| Cl— | H— | $CH_2$=$CH$—$CH_2$— | $CH_3$— | 20 | 98 |
| Cl— | H— | $OCH_3$<br>\|<br>$CH_2$—$CH_2$—$CH_2$— | $CH_3$— | 20 | 98 |
| Cl— | $CH_3$— | $CH_3$— | $CH_3$— | 20 | 98 |
| Cl— | $CH_3CH_2$— | $CH_3CH_2$— | $CH_3$— | 20 | 98 |
| Cl— | $CH_3CH_2CH_2$— | $CH_3CH_2CH_2$— | $CH_3$— | 20 | 100 |
| Cl— | $CH_3CH_2$— | $CH_3(CH_2)_2CH_2$— | $CH_3$— | 20 | 100 |
| Cl— | $CH_3$— | $OCH_2CH_3$<br>\|<br>$HC$—$CH_2$<br>\|<br>$OCH_2CH_3$ | $CH_3$— | 20 | 25 |
| Br— | H— | $(CH_3)_2CH$— | $CH_3$— | 20 | 100 |
| Br— | H— | $CH_3$—$CH_2$—$CH$—<br>\|<br>$CH_3$ | $CH_3$— | 20 | 100 |
| Br— | H— | $CH_3$<br>\|<br>$CH_3$—$C$—<br>\|<br>$CH_3$ | $CH_3$— | 20 | 100 |
| Br— | H— | $OCH_3$<br>\|<br>$CH_2$—$CH_2$— | $CH_3$— | 20 | 75 |
| Br— | $CH_3$—$CH_2$—$CH_2$— | $CH_3$—$CH_2$—$CH_2$— | $CH_3$— | 20 | 100 |
| Br— | $CH_2CH_2$— | $CH_3(CH_2)_2CH_2$— | $CH_3$— | 20 | 100 |

Table III-continued
TOBACCO SUCKER CONTROL

| R₃ | R₁ | R₂ | X | Rate mg./Plant | Tobacco Sucker Control |
|---|---|---|---|---|---|
| CH₃— | H— | CH₃—CH₂—CH— CH₃ | CH₃— | 10 | 100 |
|  |  |  |  | 50 | 100 |
| CH₃— | H— | CH₃—CH₂—CH— CH₃ | CH₃O— | 50 | 100 |
| CH₃— | H— | (CH₃)₂CH— | CH₃O— | 50 | 100 |
| CH₃— | H— | CH₃—CH₂—CH— CH₃ | CH₃—CH₂—CH—NH— CH₃ | 50 | 100 |
| (CH₃)₃CH— | H— | CH₃—CH₂—CH— CH₃ | Cl— | 50 | 98 |
| (CH₃)₃C— | H— | CH₃—CH₂—CH— CH₃ | Br— | 50 | 50 |
| (CH₃)₃C— | H— | CH₃—CH₂—CH— CH₃ | CH₃O— | 20 | 98 |
| CF₃— | CH₂CH₃— | CH₂CH₃— | NH₂— CH₃ | 20 | 100 |
| CH₃— | H— | CH₃—CH₂ CH₃—CH₂—CH₂— | | 10 | 100 |
|  |  |  |  | 50 | 100 |

EVALUATION IV

Tobacco plants of the flue-cured variety Coker 319 were transplanted to the field on May 31st.

On August 15th, the tobacco plants were in the mid-full flower stage. At this time the plants were topped and all suckers over 1 inch long were removed.

On August 16th, all chemicals were applied at a rate of 188 mg active ingredient per plant in a volume of 20 milliliters per plant.

On September 27th, suckers were harvested, counted and weighed with the following results:

Table IV

| Chemical | Rate (mg./plant) | % Sucker Control | Number of Suckers per Plant |
|---|---|---|---|
| N⁴,N⁴-diethyl-α,α,α trifluoro-3,5-dinitro-toluene-2,4-diamine | 188 | 87 | .2 |
| Check | — | 0 | 11.1 |

EVALUATION V

Tobacco plants of the flue cured variety Coker 319 were transplanted to the field on May 30th.

On July 12th, the tobacco plants were in the early midflower stage. At this time the plants were topped and all suckers over 1 inch long were removed.

On July 13th all chemicals were applied to the plants.

On July 20th all chemicals were applied to the plants for the second time.

All applications were at a rate of 63 mg. active ingredient per plant in a volume of 20 milliliters per plant.

On September 5th, suckers were harvested, counted and weighed with the following results:

Table V

| Chemical | Rate (mg./plant) | % Sucker Control | Number of Suckers per Plant | Sucker weight per plant (lbs) |
|---|---|---|---|---|
| N-(1-ethylpropyl)-2,6-dinitro-3,4 xylidine | 63 + 63 | 100 | 0 | 0 |
|  | 125 + 125 | 100 | 0 | 0 |
| N-sec-butyl-2,6-dinitro-3,4-xylidine | 63 + 63 | 85 | .2 | .5 |
|  | 125 + 125 | 91 | .1 | .3 |
| Check | 0 | 0 | 6.4 | 3.4 |

EVALUATION VI

Field Trials

A field trial was established to determine effects on a commercial tobacco variety (Pennbel-cigar wrapper type). Applications were made at two rates on an individual plant basis, with different volumes and rates per plant. The following table shows results obtained:

Table VI

| Chemical | (mg/plant) | % Sucker Control 50 cc/plant | 75 cc/plant |
|---|---|---|---|
| a,a,a-trifluoro-2,6-dinitro-N,N-dipropyl-p-toluidine | 75 | — | 68 |
|  | 100 | — | 85 |
| Dimethyl-dodecylamine acetate | 100 | 46 | — |

EVALUATION VII

Another field trial was established by spraying on a broadcast basis rather than on an individual plant basis. The method employed was as follows with the results as shown in Table VII below.

Method

Tobacco plants (variety Pennbel) were transplanted to the field on July 11 with a mechanical transplanter. All plants received starter solution plus chlordane for cutworm control. Just prior to transplanting the entire area was treated with 6 lb/A of diphenamid.

On August 12, plants were hand-topped, removing all growth to the first leaf being 6 inches wide. All suckers over 1 inch long were removed at this time. Plants were just starting to bloom at this time.

Immediately after topping, all chemicals were applied. Five plants per plot with two replications per treatment were sprayed. A single adjustable nozzle was used to deliver a coarse spray. Pressure was 20–25 lb.

All volumes sprayed resulted in good run-down to the soil line.

All plants received ½ inch overhead irrigation immediately after transplanting. For the duration of the test, all plots received a 15.9 inch rainfall plug irrigation.

Final observations were taken on September 29 and are given below in Table VII as the averages of two replications, totaling ten plants.

Table VII

| Chemical | Rate Lb/A | Percent Control | | | | | |
|---|---|---|---|---|---|---|---|
| | | Volume | | | | + .1% Triton X-100 in 100 gal/A | |
| | | 100 gal/A | | 150 gal/A | | | |
| | | %* Control | %** Red. of Sucker Length | %* Control | %** Red. of Sucker Length | %* Control | %** Red. of Sucker Length |
| 4-t-butyl-N-sec-butyl-2,6-dinitroaniline | ½ | 0 | 0 | 0 | 0 | 20 | 70 |
| " | 1 | 0 | 0 | 15 | 10 | 65 | 55 |
| " | 2 | 15 | 20 | 60 | 93 | 98 | 98 |
| α,α,α-trifluoro-2,6-dinitro-N,N-dipropyl-p-toluidine | ½ | 0 | 0 | 0 | 0 | 0 | 0 |
| " | 1 | 0 | 0 | 0 | 0 | 0 | 0 |
| " | 2 | 10 | 10 | 0 | 0 | 50 | 85 |
| Dimethyl dodecylamine acetate | 1½ | 10*** | 30 | — | — | — | — |
| Maleic hydrazide | 3 | 98 | 98 | — | — | — | — |

*% Control - reduction in number of suckers over 4" in length.
**% Height reduction - % decrease in length of suckers of the plant.
***Applied in volume of 50 gal/A.

Although the mechanism involved in sucker control with these compounds is unknown, it would appear that effects are achieved by inhibiting growth of the sucker without killing it. As described above, and as confirmed by the results set out in Table VII, the addition of a wetting agent or surfactant to the solution of the active sucker control compound in water significantly enhances the sucker controlling activity of the compound.

To obtain maximum efficiency from the substituted dinitroanilines it is preferred to use:
1. High volumes per acre (100 gal. and above) to insure adequate coverage and run-down to each leaf axil.
2. The addition of a surfactant, e.g., Triton X-100, at .1% volume.
3. Rates of about 2 lb/A.
4. Sprayer adjusted to deliver a coarse spray, thereby facilitating run-down with low pressures.

EVALUATION VIII

Field Test with Surfactant Added

Tobacco plants (variety Pennbel) were transplanted to the field on June 10th with a mechanical transplanter. All plants received starter solution plus chlordane for cutworm control.

Just prior to transplanting, the entire plot area was treated with 6 lb/A diphenamid.

On August 17th, all plants were hand-topped, removing all growth to the first leaf being 6 inches wide. All suckers over 1 inch in length were removed at this time.

On August 18th, all treatments were applied. A single adjustable cone nozzle, set for a very coarse spray, was used with pressure held at 20–25 lbs. Treatments of maleic hydrazide were applied in a fine spray pattern.

Final observations were taken on September 11th, 24 days after treatments were applied.

Readings are averages of 3 replications totaling 15 plants per treatment.

In all cases, the 4 lb/gal. formulation of 4-t-butyl-N-sec-butyl-2,6-dinitroaniline was used, along with commercial formulations of trifuluralin, maleic hydrazide (MH-30) and dimethyl dodecylamine acetate (Penar).

Volume of application did not appear to be critical within the ranges tested (100 gal/A; 150 gal/A; 200 gal/A) with control being essentially the same at 100 gal/A as with 200 gal/A. The 100 gal/A volume provided excellent run-down to the soil line.

Table VIII

| Chemical | Rate lb/A | Percent Control* | | | | | |
|---|---|---|---|---|---|---|---|
| | | No Surfactant | | | + 0.1% Triton X-100 | | |
| | | 100 gal/A | 150 gal/A | 200 gal/A | 100 gal/A | 150 gal/A | 200 gal/A |
| 4-t-butyl-N-sec-butyl-2,6-dinitroaniline | ½ | 28 | 22 | 38 | 65 | 69 | 67 |
| " | 1 | 29 | 21 | 55 | 81 | 75 | 83 |
| " | 1½ | 40 | 58 | 71 | 91 | 86 | 88 |
| " | 2 | 57 | 68 | 65 | 88 | 92 | 92 |
| " | 3 | 76 | 84 | 74 | 90 | 99 | 99 |

Table VIII-continued

| | | Percent Control* | | | | | |
|---|---|---|---|---|---|---|---|
| | | No Surfactant | | | + 0.1% Triton X-100 | | |
| Chemical | Rate lb/A | 100 gal/A | 150 gal/A | 200 gal/A | 100 gal/A | 150 gal/A | 200 gal/A |
| α,α,α-tri-fluoro-2,6-dinitro-N,N-dipropyl-p-toluidine | 1 | — | 48 | — | — | 79 | — |
| " | 2 | — | 60 | — | — | 74 | — |
| " | 3 | — | 81 | — | — | 90 | — |
| Maleic hydrazide | 3 | 66 | — | — | — | — | — |
| Dimethyl dodecylamine acetate | 1½ | 62 | — | — | — | — | — |

*Percent Control = percent by which treatment reduced sucker green weight compared with topped but not suckered check.

EVALUATION IX

Field Tests with Combination Products: Combination with $C_6$ to $C_{18}$ Fatty Alcohol A field trial was established to determine the effects of the combination product consisting of a dinitroaniline derivative and a $C_6$ to $C_{12}$ fatty alcohol, on different tobacco varieties. Tobacco plants of the Burley type (variety Burley 21), Flue Cured type (Variety Coker 254), Maryland type (variety Maryland 10) and Cigar Filler type (variety Pennbel 69) were transplanted to the field with a mechanical transplanter. All plants received starter solution plus chlordane for cutworm control. Just prior to transplanting the entire area, it was treated with 6 lbs. per acre of diphenamid.

All plants were hand topped, removing all growth to the first elaf, being six inches wide. All suckers over one inch (1 inch) in length were removed at this time.

Immediately after topping, all ;eatments were effected. A single adjustable cone nozzle, set for a very coarse spray, was used with pressure held at 15 lbs.

Final observations were taken after prolonged periods of time as follows:

25 days after treatment on the Burley type.
45 days after treatment on the Flue Cured type.
41 days after treatment on the Maryland type.
30 days after treatment on the Cigar type.

Readings are averages of 4 replications totaling 10 plants per treatment.

A 3 lb/gal. formulation of 4-t-butyl-N-sec-butyl-2,6-dinitroaniline containing surfactant was employed on control plants at the rates of application indicated in Table IX. A 4.7 lb/gal. formulation of a known commercial formulation (Off-Shoot-T) fatty alcohol tobacco sucker agent, having the following composition of active ingredients: $C_6$-.5% by weight, $C_8$-42% by weight, $C_{10}$-56% by weight, $C_{12}$-1.5% by weight and, in addition, an effective amount of a surfactant was employed to control plants at the rates of application indicated in Table IX.

Formulations of 4-t-butyl-N-sec-butyl-2,6-dinitroanilne containing surfactant were used in combination with the $C_6$-$C_{12}$ fatty alcohol tobacco sucker agent. The admixture formulation was prepared by mixing emulsifiable concentrate of the 4-t-butyl-N-sec-butyl-2,6-dinitroaniline to the emulsifiable concentrate of the fatty alcohol, and adding water to make the desired volume of ready-to-use emulsion. The volume of application was 50 gal/acre and the particular rates of application are listed in Table IX.

Table IX

| | | Percent Control | | | |
|---|---|---|---|---|---|
| | | Types of Tobacco | | | |
| Chemical | Rate lb/A | Burley | Flue Cured | Mary-land | Cigar |
| 4-t-butyl-N-sec-butyl-2,6-dinitroaniline | | | | | |
| " | ½ | 28 | — | 4 | 9 |
| " | 1 | 50 | 18 | 32 | 34 |
| " | 2 | 72 | 20 | 55 | 74 |
| " | 3 | 80 | 18 | 78 | 70 |
| " | 6 | 90 | — | 83 | 92 |
| Fatty alcohol | | | | | |
| " | 6 | — | — | — | 4 |
| " | 7 | — | — | 10 | — |
| " | 10 | — | — | — | 41 |
| " | 12 | 47 | 10 | — | 54 |
| " | 14 | 51 | — | 51 | — |
| 4-t-butyl-N-sec-butyl-2,6-dinitroaniline + Fatty alcohol | | | | | |
| " | ½ + 2 | — | — | — | 47 |
| " | ½ + 4 | — | — | — | 67 |
| " | ½ + 6 | 94 | — | — | 74 |
| " | 1 + 2 | — | — | — | 60 |
| " | 1 + 4 | — | — | — | 74 |
| " | 1 + 6 | — | — | — | 91 |
| " | 1 + 7 | — | — | 93 | — |
| " | 1 + 9 | 97 | — | — | — |
| " | 2 + 12 | 98 | 92 | — | — |

On each type of tobacco employed, it will be observed from Table IX that a better than additive result is obtained by employing the admixture composition and for especially prolonged periods of time, i.e., at least 25 days after treatment, the sucker control is more effective than was previously observed by the use of either of the two agents alone.

EVALUATION X

Another field trial was run to determine the effects on tobacco of the combination product consisting of a dinitroaniline derivative and $C_6$ to $C_{12}$ fatty alcohols. The trial was also intended to compare the activity of the combination product in the form of a simple tank mix of the two components, as against the combination product in the form of a one-package formulation with the following composition: 4-tert-butyl-N-sec-butyl-2,6-dinitroaniline - 9.8% by weight; $C_6$ to $C_{12}$ fatty alcohols - 59% by weight; surfactant - 29.5% by weight; with the remainder comprised of xylene and inert ingredients.

The trial was set up in a commercial field in Comerio, Puerto Rico, and the tobacco variety used was Puerto Rico 5. The type tobacco is handled in much the same way as flue-cured varieties in the United States, except that it is naturally cured. Harvesters go through the field from 5 to 7 times at weekly intervals, harvesting from 3 to 4 leaves from each plant. This harvesting also includes priming of the remaining leaves by removing any large suckers present. The first three primings are taken prior to hand-topping the plant which, at the time of topping, has usually reached the button to early flower stage. In this trial the tobacco plants were hand-topped on December 17, at which time the plants were approximately 3½ to 4 feet tall. Immediately after topping, all chemcials were applied as a coarse spray to each individual plant. A volume of 20 ml per plant provided very good run-down to the soil line. A single nozzle hand-boom was used with an adjustable cone nozzle set to deliver a very coarse spray. Pressure was maintained at 15 lbs. Each treatment was applied to 10 plants with one replication per treatment. On January 14, final sucker control evaluations were made by counting and weighing the suckers from each individual plant. The results achieved are set out in Table X below:

Table X

| Chemical | mg/Plant | % Sucker Control | Suckers per Plant | Weight per Sucker (g) | Injury |
|---|---|---|---|---|---|
| 4-tert-butyl-N-sec-butyl-2,6-dinitro-aniline | 126 | 96 | 0.8 | 32.0 | 0 |
| " | 180 | 87 | 1.2 | 69.4 | 0 |
| " | 250 | 73 | 2.0 | 83.0 | 0 |
| Fatty Alcohol | 756 | 0 | 4.4 | 157.3 | 0 |
| " | 1512 | 18 | 3.7 | 137.4 | 0 |
| 4-tert-butyl-N-sec-butyl-2,6-dinitro-aniline + Fatty Alcohol as a Tank Mix | 126 + 756 | 94 | 0.5 | 76.2 | 0 |
| " | 250 + 756 | 97 | 0.3 | 64.7 | 0 |
| " | 126 + 1512 | 93 | 0.5 | 80.4 | 0 |
| " | 250 + 1512 | 99 | 0.1 | 85.0 | 0 |
| 4-tert-butyl-N-sec-butyl-2,6-dinitro-aniline + Fatty Alcohol as a One-Package Formulation | 126 + 756 | 99 | 0.2 | 17.0 | 0 |
| " | 250 + 1512 | 96 | 0.2 | 12.4 | 0 |
| Check | — | 0 | 5.0 | 124.0 | 0 |

EVALUATION XI

Another field trial, similar to the one described immediately above, but using lower rates of chemical, was conducted in Comerio, Puerto Rico. The plants were 5 feet tall at the time of application and had already been primed twice. Application was made as a coarse spray at the rate of 20 ml per plant immediately after topping on January 14. Each treatment was replicated on 5 plants. Final sucker control evaluations were made on February 1. The results are set out in Table XI below.

Table XI

| Chemical | mg/Plant | % Sucker Control | Suckers per Plant | Weight per Sucker (g) | Injury |
|---|---|---|---|---|---|
| 4-tert-butyl-N-sec-butyl-2,6-dinitro-aniline | 63 | 89 | 0.6 | 15.2 | 0 |
| " | 90 | 67 | 0.8 | 34.1 | 0 |
| " | 125 | 100 | 0.0 | 0.0 | 0 |
| Fatty Alcohol | 378 | 0 | 5.0 | 30.0 | 0 |
| " | 756 | 0 | 3.4 | 32.1 | 0 |
| 4-tert-butyl-N-sec-butyl-2,6-dinitro-aniline + Fatty Alcohol as a Tank Mix | 63 + 378 | 100 | 0 | 0 | 0 |
| " | 125 + 378 | 100 | 0 | 0 | 0 |
| " | 63 + 756 | 100 | 0 | 0 | 0 |
| " | 125 + 756 | 100 | 0 | 0 | 0 |
| 4-tert-butyl-N-sec-butyl-2,6-dinitro-aniline + Fatty Alcohol as a One-Package Formulation | 63 + 378 | 100 | 0 | 0 | 0 |
| " | 125 + 756 | 100 | 0 | 0 | 0 |
| Check | — | 0 | 3.2 | 25.5 | 0 |

EVALUATION XII

Field Tests with Combination Products: Combination with $C_6$ to $C_{18}$ Fatty Acid Amines A field test was effected to determine the activity of a combination product consisting of a dinitroaniline derivative and dimethyl-dodecylamine acetate. Tobacco plants of the Burley type (variety Burley 21) and Cigar Filler type (variety Pennbel 69) were transplanted to the field with a mechanical transplanter. All plants received starter solution plus chlordane for cutworm control. Just prior to transplanting, the entire area was treated with 6 lbs./acre diphenamid.

All plants were hand-topped, removing all growth to the first leaf being six inches wide. All suckers over one inch in length were removed at this time.

Immediately after topping, all treatments were effected. A single adjustable cone nozzle was used with pressure held at 15 lbs.

Final observations were taken 25 days after treatment for the Burley type and 30 days after treatment for the Cigar type. Readings are averages of 4 replications totaling 10 plants per treatment.

A 3-lb./gal. formulation of 4-t-butyl-N-sec-butyl-2,6-dinitroaniline was employed on control plants at the rates of application indicated in Table XII. A 4-lb./gal. formulation of dimethyl-dodecylamine acetate (Penar) was employed on control plants at the rates of application indicated in Table XII.

Formulations of 4-t-butyl-N-sec-butyl-2,6-dinitroaniline in combination with dimethyl-dodecylamine acetate (Penar) were employed. The admixture formulations were prepared by mixing the emulsifiable concentrate of the 4-t-butyl-N-sec-butyl-2,6-dinitroaniline to the emulsifiable concentrate of the dimethyl-dodecylamine acetate, thereafter adding water to make the desired volume of ready-to-use emulsion. The volume of application was 50 gal/acre and the rates of application are listed in Table XII.

Table XII

| | | Percent Control Types of Tobacco | |
|---|---|---|---|
| Chemical | Rate lb/A | Burley | Cigar |
| 4-t-butyl-N-sec-butyl-2,6-dinitroaniline | | | |
| " | ½ | 28 | 9 |
| " | 1 | 50 | 34 |
| " | 2 | 72 | 74 |

Table XII-continued

| Chemical | Rate lb/A | Percent Control Types of Tobacco | |
|---|---|---|---|
| | | Burley | Cigar |
| " | 3 | 80 | 70 |
| " | 6 | 90 | 92 |
| Dimethyl-dodecylamine Acetate | | | |
| " | ¼ | — | 0 |
| " | ½ | — | 0 |
| " | ¾ | — | 29 |
| " | 1 | — | 27 |
| " | 1½ | 46 | 33 |
| " | 3 | 78 | 55 |
| 4-t-butyl-N-sec-butyl-2,6-dinitroaniline + Dimethyl-dodecylamine Acetate | | | |
| " | ¼ + ¼ | — | 39 |
| 4-t-butyl-N-sec-butyl-2,6-dinitroaniline + Dimethyl-dodecylamine Acetate | | | |
| " | ½ + ¾ | — | 39 |
| " | 1 + ¼ | — | 56 |
| " | 1 + ½ | — | 31 |
| " | 1 + ¾ | — | 54 |
| " | 1 + 1 | 90 | — |
| " | 2 + 1½ | 93 | — |

The preparation and use of the novel compounds of this invention will be further understood from the following specific examples which are intended by way of illustration only.

EXAMPLE 1

Following the method of Dutton, et al, (Canadian Journal of Chemistry, Volume 31, p. 685, 1953), 200 grams (1.32 moles) 4-t-butylphenol was dissolved in 480 ml. glacial acetic acid and added dropwise over a period of one hour to a stirred solution of 320 ml. of 90% nitric acid and 600 ml. of glacial acetic acid at −10 to −15° C. After complete addition, the temperature rises to 0 to −5° C. The reaction mixture is then allowed to come to room temperature and maintained there for one hour. The mixture is then poured onto cracked ice, diluted with water and cooled. The product is then filtered, washed with $H_2O$, dried and recrystallized from hot hexane to give 180 grams of 2,6-dinitro-4-t-butylphenol in the form of fine yellow needles melting at 94°–95° C.

180 grams (.75 mole) of 2,6-dinitro-4-t-butylphenol thus prepared was placed in a mixture of 113 grams (.95 mole) thionyl chloride, 55 grams (0.76 mole) dimethylformamide and 300 ml. of dry toluene. The mixture was stirred and heated to reflux temperature for 15 hours, after which time the thionyl chloride, DMF and toluene were removed under reduced pressure until a slush remained. Hexane was then added to the reaction vessel, the mixture cooled and filtered. The product was then recrystallized from boiling hexane to give 168 grams 2,6-dinitro-4-t-butylchlorobenzene in the form of light yellow needles melting at 114°–116° C.

EXAMPLE 2

One gram of 2,6-dinitro-4-t-butylchlorobenzene was allowed to react with one gram of sec-butylamine by adding the amine dropwise to a refluxing mixture of 50 ml. dry toluene, and the 2,6-dinitro-4-t-butylchlorobenzene. After complete addition, the mixture was refluxed eight hours, cooled to room temperature, the amine hydrochloride filtered off, and toluene and unreacted amine were removed under reduced pressure. The thick material that resulted was dissolved in hot ethanol and the product was crystallized upon cooling to yield N-sec-butyl-2,6-dinitro-4-t-butylaniline melting at 60°–62° C.

EXAMPLE 3

Two and six-tenths grams (.01 mole) of 2,6-dinitro-4-t-butylchlorobenzene was reacted with 3.1 grams of 40% aqueous solution of dimethylamine in 50 ml. ethanol. The temperature was slowly increased as follows: 30° C. for 1 hour, 40° C. for 1 hour, 50° C. for one hour, then 80° C. for five hours. When the reaction was complete, about 100 ml. $H_2O$ was added, precipitating the product. This was filtered, washed with portions of $H_2O$ and upon recrystallization from ethanol yielded 2.5 grams of N,N-dimethyl-2,6-dinitro-4-t-butylaniline in the form of orange-yellow needles melting at 101–102° C.

Following the above procedure, two grams of 40% aqueous solution of methyl amine was reacted with 2.6 grams of 2,6-dinitro-4-t-butyl-chlorobenzene to give N-methyl-2,6-dinitro-4-t-butylaniline as orange needles melting at 129°–130° C.

Following the above procedure, two grams of a 70% aqueous solution of ethylamine was reacted with 2.6 grams (0.01 mole) of 2,6-dinitro-4-t-butylchlorobenzene to yield 2 grams of N-ethyl-2,6-dinitro-4-t-butylaniline as orange needles melting at 70°–73° C.

EXAMPLE 4

| | 2 lb/gal Emulsifiable Concentrate | |
|---|---|---|
| Chemical | Lbs. | % by Wt. |
| N-s-butyl-4-t-butyl-2,6-dinitroaniline | 2.02 | 23.40 |
| Atlox 3387 | 1.00 | 11.59 |
| Panasol AN-3 | 5.61 | 65.01 |

Manufacturing Directions: Combine ingredients and stir to a homogenous solution.

EXAMPLE 5

| Chemical | Lbs. | % by Wt. |
|---|---|---|
| N-s-butyl-4-t-butyl-2,6-dinitroaniline | 4.244 | 50.48 |
| Toximul D | 0.420 | 5.00 |
| Dimethylformamide | 0.999 | 11.88 |
| Xylene (0.868 at 20° C. | 2.745 | 32.64 |
| | 8.408 | 100.00 |

Specific Gravity: 1.010 at 20° C.
Manufacturing Directions: Add ingredients and stir until solution is achieved and specific gravity is correct.

EXAMPLE 6

A liquid concentrate that is diluted with water prior to application has the following composition:

| | Gallon | lb/gal. | % Wt. |
|---|---|---|---|
| N-s-butyl-4-t-butyl-2,6-dinitroaniline (95%) | — | 0.80 | 10.5 |
| Fatty alcohols ($C_8$ and $C_{10}$-98% by wt.; $C_6$ and $C_{12}$-2% by wt.) | 0.65 | 4.50 | 59.0 |
| Ethoxylated sorbitol monooleate (surfactant) | 0.25 | 2.25 | 29.5 |
| Xylene | 0.01 | 0.08 | 1.0 |
| | 1.00 | 7.63 | 100.0 |

Addition of water to the concentrate results in a final product in the form of an emulsion.

We claim:

1. A method of inhibiting the growth of suckers on tobacco plants which comprises applying to the tobacco plants an effective amount of a compound of the formula:

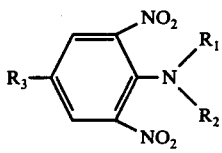

wherein $R_1$ and $R_2$ are each independently selected from the group consisting of:
(a) hydrogen,
(b) lower alkyl,
(c) halo-substituted-lower alkyl,
(d) lower alkenyl,
(e) alkoxy-lower alkyl, and
(f) monocycloalkyl-lower alkyl, with the proviso that only one of $R_1$ and $R_2$ can be branched lower alkyl or branched lower alkenyl;

wherein $R_3$ is selected from the group consisting of:
(a) halo,
(b) lower alkyl,
(c) halo-substituted-lower alkyl,
(d) methylsulfonyl, and
(e) sulfanilamide;

with the proviso that $R_1$ and $R_2$ cannot both be hydrogen and that one of $R_1$ and $R_2$ may only be hydrogen when:
(a) $R_2$ is alkoxy-lower alkyl, or
(b) $R_3$ is halo-substituted lower alkyl.

2. The method of claim 1, wherein the compound is contained in an aqueous emulsion.

3. The method of claim 1, further comprised of applying in admixture with the compound between about 0.33 and about 3 parts by weight of surfactant per part by weight of the compound.

4. A method of inhibiting the growth of suckers on tobacco plants which comprises applying to the tobacco plants an effective amount of a compound of the formula:

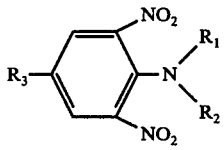

wherein $R_1$ and $R_2$ are each independently selected from the group consisting of:
(a) lower alkyl,
(b) halo-substituted lower alkyl,
(c) lower alkenyl,
(d) alkoxy-lower alkyl, and
(e) monocycloalkyl-lower alkyl, with the proviso that only one of $R_1$ and $R_2$ can be branched lower alkyl or branched lower alkenyl;

wherein $R_3$ is selected from the group consisting of:
(a) halo,
(b) lower alkyl,
(c) halo-substituted-lower alkyl,
(d) methylsulfonyl, and
(e) sulfanilamide.

5. The method of claim 4, wherein $R_1$ and $R_2$ are independently selected from the group consisting of:
(a) lower alkyl,
(b) halo-substituted lower alkyl,
(c) monocycloalkyl-lower alkyl; and $R_3$ is selected from the group consisting of:
(a) lower alkyl, and
(b) halo-substituted lower alkyl.

6. The method of claim 4, wherein the compound is $\alpha,\alpha,\alpha$-trifluoro-2,6-dinitro-N,N-dipropyl-p-toluidine.

7. The method of claim 4, wherein the compound is N-butyl-N-ethyl-$\alpha,\alpha,\alpha$-trifluoro-2,6-dinitro-p-toluidine.

8. The method of claim 4, wherein the compound is 2,6-dinitro-N,N-dipropylcumidine.

9. The method of claim 4, wherein the compound is 4(methylsulfonyl)-2,6-dinitro-N,N-dipropylaniline.

10. The method of claim 4, wherein the compound is 3,5-dinitro-$N^4,N^4$-dipropylsulfanilamide.

11. The method of claim 4, wherein the compound is N-(cyclopropylmethyl)-$\alpha,\alpha,\alpha$-trifluoro-2,6-dinitro-N-propyl-p-toluidine.

12. The method of claim 4, wherein the compound is N-(2-chloroethyl)-2,6-dinitro-N-propyl-$\alpha,\alpha,\alpha$-trifluoro-p-toluidine.

13. The method of claim 4, wherein the compound is N,N-bis-(2-chloroethyl)-2,6-dinitro-p-toluidine.

14. The method of claim 4, wherein the compound is contained in an aqueous emulsion.

15. The method of claim 4, further comprised of applying in admixture with the compound between about .33 and about 3 parts by weight of surfactant per part by weight of the compound.

16. A method of inhibiting the growth of suckers on tobacco plants which comprises applying to the tobacco plants an effective amount of a compound of the formula:

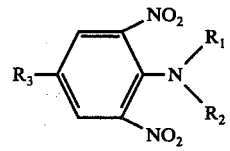

wherein $R_1$ and $R_2$ are each independently selected from the group consisting of:
(a) hydrogen,
(b) lower alkyl,
(c) halo-substituted-lower alkyl,
(d) lower alkenyl,
(e) alkoxy-lower alkyl, and
(f) monocycloalkyl-lower alkyl, with the proviso that only one of $R_1$ and $R_2$ can be branched lower alkyl or branched lower alkenyl;

wherein $R_3$ is selected from the group consisting of:
(a) halo,
(b) lower alkyl,
(c) halo-substituted-lower alkyl,
(d) methyl sulfonyl, and
(e) sulfanilamide;

with the proviso that when $R_2$ is hydrogen and $R_1$ is hydrogen, lower alkyl, lower alkenyl or monocycloalkyl-lower alkyl, then $R_3$ may not be lower alkyl.

17. The method of claim 16, wherein the compound is contained in an aqueous emulsion.

18. The method of claim 16, further comprised of applying in admixture with the compound between about 0.33 and about 3 parts by weight of surfactant per part by weight of the compound.

* * * * *

UNITED STATES PATENT OFFICE
CERTIFICATE OF CORRECTION

Patent No. 4,077,795   Dated March 7, 1978

Inventor(s) A.R. Cooke and G.R. Starke

It is certified that error appears in the above-identified patent and that said Letters Patent are hereby corrected as shown below:

Column 4, line 17 "OR" should be "of".

Column 19, line 20, "plug" should be "plus".

Column 26, line 36, the following was omitted and should be inserted "Specific Gravity: 1.037 at 20°C."

Signed and Sealed this

Twenty-second Day of August 1978

[SEAL]

Attest:

RUTH C. MASON
Attesting Officer

DONALD W. BANNER
Commissioner of Patents and Trademarks